United States Patent [19]

Halczenko et al.

[11] Patent Number: 4,751,231
[45] Date of Patent: Jun. 14, 1988

[54] SUBSTITUTED THIENO[2,3-B]PYRROLE-5-SULFONAMIDES AS ANTIGLAUCOMA AGENTS

[75] Inventors: Wasyl Halczenko, Hatfield; George D. Hartman, Lansdale, both of Pa.

[73] Assignee: Merck & Co., Inc., Rahway, N.J.

[21] Appl. No.: 96,999

[22] Filed: Sep. 16, 1987

[51] Int. Cl.$^4$ ................. A61K 31/445; C07D 487/02
[52] U.S. Cl. .................... 514/412; 514/253; 514/321; 514/233.8; 544/144; 544/373; 546/198; 548/453
[58] Field of Search ............. 514/412, 229, 253, 321; 548/453; 549/50, 55, 65; 546/198; 544/373, 144

[56] References Cited

U.S. PATENT DOCUMENTS

| 4,477,466 | 10/1984 | Shepard | 549/65 |
| 4,668,697 | 5/1987 | Shepard | 549/55 |

FOREIGN PATENT DOCUMENTS 2565981 12/1985 France ................. 548/453

OTHER PUBLICATIONS

Snyder et al., J. Amer. Chem. Soc., 1957, 79, 2556.
Kumar et al., Ind. J. Chem., 1981, 20B, 271.

*Primary Examiner*—Alan Siegel
*Attorney, Agent, or Firm*—William H. Nicholson; Michael C. Sudol

[57] ABSTRACT

Thieno[2,3-b]pyrrole-5-sulfonamides are carbonic anhydrase inhibitors useful in the treatment of elevated intraocular pressure and glaucoma.

8 Claims, No Drawings

SUBSTITUTED THIENO[2,3-B]PYRROLE-5-SULFONAMIDES AS ANTIGLAUCOMA AGENTS

SUMMARY OF THE INVENTION

This invention relates to novel aromatic sulfonamides useful in the treatment of elevated intraocular pressure. More particularly this invention relates to compounds having the structural formula:

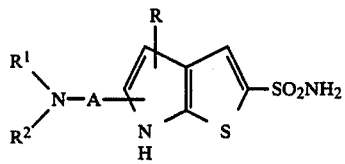

wherein A, R, $R^1$, and $R^2$ are as hereinafter defined, as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma. The invention also relates to processes for preparation of the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that render these agents unacceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

DETAILED DESCRIPTION OF THE INVENTION

The novel compounds of this invention have structural formula:

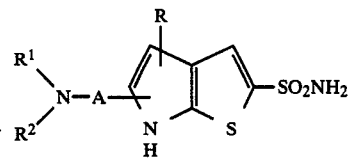

or a pharmaceutically acceptable salt thereof, wherein
A is $C_{1-8}$ alkylene, either straight or branched chain and either unsubstituted or substituted with $C_{1-3}$ alkoxy or hydroxy; and
R is hydrogen or $C_{1-6}$ alkyl, either straight or branched chain; and
$R^1$ and $R^2$ are independently:
 (1) hydrogen,
 (2) $C_{1-6}$ alkyl, either unsubstituted or substituted with one or more of
  (a) $C_{1-3}$ alkoxy,
  (b) hydroxy,
  (c) phenyl, or
  (d) $-NR^3R^4$ wherein $R^3$ and $R^4$ are independently selected from
   (i) hydrogen and
   (ii) $C_{1-6}$ alkyl, either unsubstituted or substituted with one or more of $C_{1-3}$ alkoxy, hydroxy or phenyl, or
 (3) taken together with the nitrogen atom to which they are attached form a 5 to 7 membered heterocycle such as piperidine, morpholine, piperazine, or N—$C_{1-3}$ alkylpiperazine.

A preferred embodiment of the novel compounds is that wherein A is joined to the 2-position of the thieno[2,3 b]pyrrole ring system.

It is still more preferred that A is $-(CH_2)-_{1-3}$, especially $-CH_2-$.

It is also preferred that $R^1$ is hydrogen, and that $R^2$ is $C_{1-6}$ alkyl.

The novel processes for preparing the novel compounds of this invention are illustrated by reaction Scheme I.

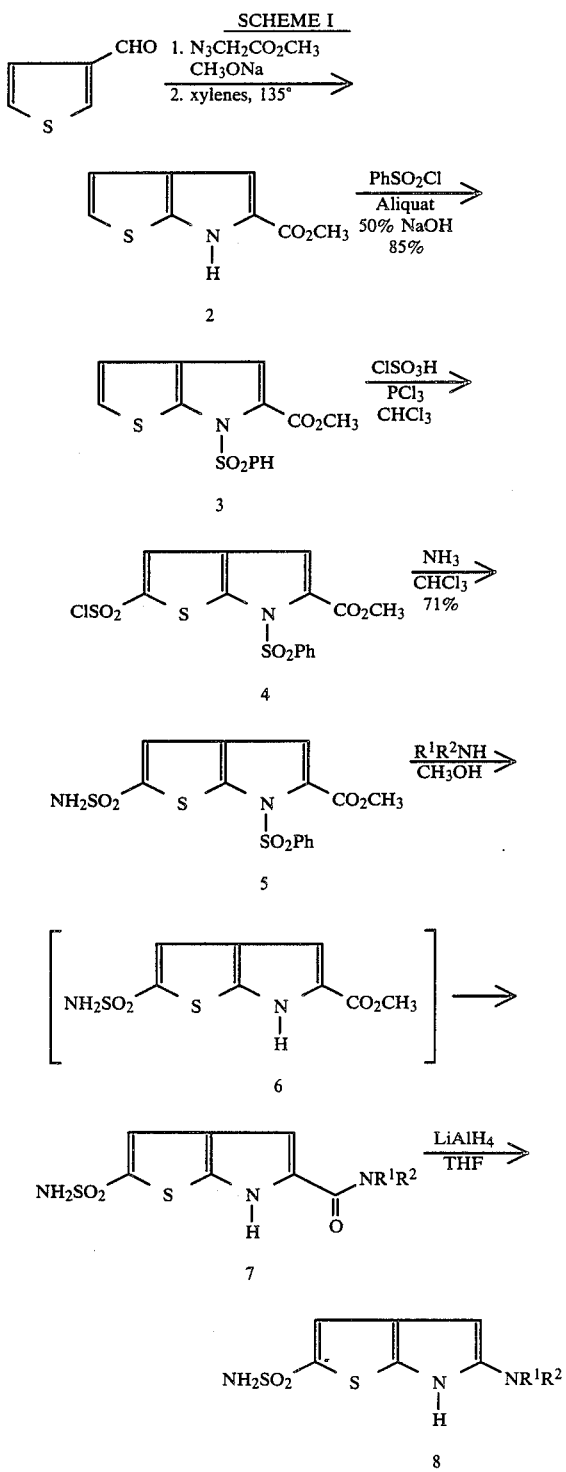

SCHEME I

The known compound 2 is treated with phenylsulfonyl chloride at about 15° to 30° C. under phase transfer conditions for about 0.5 to 6 hours to provide 3. Treatment of 3 in a halocarbon such as chloroform at about 0°–10° C. under standard chlorosulfonating conditions for about 0.5 to 2 hours provides after hydrolytic workup the desired chlorosulfonated derivative 4. Ammonolysis of 4 with ammonia, preferably in chloroform solution at 0°–10° C. for about 0.5 to 2 hours gives sulfonamide 5. On treatment of 5 with a methanolic solution of an amine, $RNH_2$, and sodium methoxide, the phenylsulfonyl group is rapidly cleaved to give 6 which is slowly converted over 3 to 7 days under the above conditions to the desired amide 7. Treatment of 7 with lithium aluminum hydride in refluxing THF over the course of 1 to 3 days provides the aminomethyl product 8.

The novel pharmaceutical formulations of this invention are adapted for topical ocular administration in the form of solutions, ointments, solid water soluble polymeric inserts, or solutions which gel at body temperature or in the presence of lachrymal fluids for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of an effective amount of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

2-(Methylaminomethyl)thieno[2,3-b]pyrrole-5 sulfonamide hydrochloride

Step A: Preparation of Methyl 1-phenylsulfonylthieno[2,3 b]pyrrole-2-carboxylate (3)

To a mechanically stirred mixture of 0.5 g (2.76 mmole) 2, 1.4 g (2.76 mmole) Aliquat-336, and 1.0 g (5.68 mmole) phenylsulfonyl chloride was added 5 mL of a 50% aqueous sodium hydroxide solution at room temperature. After stirring for 0.5 hour, the reaction mixture was diluted with 25 mL water/50 mL chloroform. The organic phase was separated, washed with 3×20 mL portions of water, brine, and dried. The solution was passed through a silica gel pad and the solvent was removed in vacuo to give a semi-solid. This was triturated with cold hexane and filtered to give 0.75 g (85%) of 3 as a tan solid, m.p. 165°–167°; NMR (deuteriochloroform): δ3.68 (3H, s), 7.00 (1H, d, J=8 Hz), 7.10 (1H d, J=8 Hz), 7.29 (1H, s), 7.59 (3H, m), 8.06 (2H, d, J=8, 1 Hz); ms: m/e 321.

Step B: Preparation of Methyl (1 phenylsulfonyl-5-chlorosulfonyl)thieno[2,3 b]pyrrole-2-carboxylate (4)

To a solution of 0.52 g (2.5 mmole) phosphorus pentachloride in 0.73 g (6.3 mmole) chlorosulfonic acid under nitrogen and cooled to 0°–10° was added a solution of 0.80 g (2.5 mmole) 3 in 10 mL chloroform dropwise. After stirring for 0.5 hour the reaction was quenched with ice and was then extracted with 4×25 mL portions of chloroform. The combined organic phases were washed with brine, dried and the solvent was removed in vacuo to give an amber oil. This was triturated with ether to provide 0.60 g (60%) of 4 as a tan solid; m.p. 165°-180° dec.; NMR (deuteriochloroform): δ3.80 (3H, s), 7.39 (1H, d, J=1 Hz , 7.60 (2H, t), 7.72 (1H, t), 7.90 (1H, s), 8.10 (2H, dd, J=8, 1 Hz); ms: m/e 419.

Step C: Preparation of Methyl (1-phenylsulfonyl-5-sulfamoyl)thieno[2,3-b]pyrrole-2-carboxylate (5)

Gaseous ammonia was bubbled into a solution of 5.10 g (12.0 mmole) 4 in 250 mL chloroform cooled to 0°-10° for 10 minutes. The reaction mixture was stirred for 0.5 hour and then the solvent was removed in vacuo. The residue was taken up in 100 mL ethyl acetate/50 mL water. The organic phase was separated, washed with water, brine, dried, and passed through a silica gel pad. The solvent was removed in vacuo to provide 3.84 g (71%) of 5 as a white solid, m.p. 197°-199°; NMR (DMSO-$d_6$) δ7 3.72 (3H, s), 7.55 (1H, d J=2 Hz), 7.79 (3H, m), 7.98 (2H, dd, J=8, 1 Hz); ms: m/e 301.

Step D: Preparation of N-Methyl 5-sulfamoylthieno[2,3-6]pyrrole-2-carboxamide (7, R=CH₃)

Gaseous monomethyl amine was bubbled into 40 mL methanol cooled to 0°- ° for 10 minutes. To this was added 3.0 g (7.5 mmole) 5 followed by 5 mg sodium metal and the resulting solution was stirred under nitrogen for 4 days. The solvent was removed in vacuo and after adding 50 mL water, the pH was adjusted to 8-9 with 6N HCl. Upon cooling and stirring at 0°-10° a tan solid appeared. This was collected and washed with water to give 1.85 g (95%) 7(R=CH₃) m.p. >260° (dec); NMR (DMSO-$d_6$): δ3.32 (3H, s), 7.05 (1H, d, J=2 Hz), 7.55 (3H, m), 8.31 (1H, m).

Step E: Preparation of 2-(Methylaminomethyl)thieno[2,3-b]pyrrole-5-sulfonamide hydrochloride (8, R=CH₃)

To a suspension of 1.37 g (0.036 mole) lithium aluminum hydride in 150 mL of THF at room temperature was added 1.56 g (0.006 mole) 7 (R =CH₃) in 150 mL of THF dropwise and the resulting mixture was heated at reflux. After 22 hours the reaction mixture was cooled and quenched with 50 mL of a saturated Na⁺-K⁺ tartrate solution. After adjusting the pH of this mixture to 8-9 with dilute HCl, it was extracted with 5×200 mL portions of ethyl acetate. The combined organic extracts were washed with brine, dried and the solvent removed in vacuo. The residue was taken up in 3N HCl (50 mL) and extracted with ethyl acetate to remove the unreacted 7 (R=CH₃). The aqueous phase was rendered basic (pH 8-9) and extracted with 5×50 mL portions of ethyl acetate. The combined organic extracts were washed with brine, dried and the solvent removed in vacuo to provide the free base of 8 (R=CH₃) as a yellowish solid, 0.25 g, 17% yield. This material was converted to 8 (R=CH₃) by treatment with excess ethanolic HCl in a mixture of ethanol (15 mL) methanol (5 mL) to provide 0.15 g of 8 (R=CH₃) as a tan solid. Recrystallization from ethanol gave material with m.p. 210°-212° (dec.), NMR (DMSO-$d_6$): δ1.50 (3H, d), 4.20 (2H, bs), 6.58 (1H, d, J=2 Hz), 7.49 (1H, s), 7.53 (2H, bs, SO₂NH₂), 9.0 (2H, bs, NH₂⁺), 11.50 (1H, bs, NH).

Anal. Calc'd for C₈H₁₁N₃O₂S HCl: C, 34.10; H, 4.29; N, 14.91. Found: C, 34.48; H, 4.52; N, 14.68.

EXAMPLE 2
2-(Isobutylaminomethyl)thieno[2,3-b]pyrrole-5 sulfonamide hydrochloride

Step A: Preparation of N-Isobutyl-5-sulfamoylthieno[2,3-b]pyrrole-2-carboxamide (7, R=iBu)

A solution of 3.0 g (7.5 mmole) 5 in 30 mL isobutylamine was heated at reflux for 24 hours. Excess amine was removed in vacuo and after the addition of 50 mL water, the pH was adjusted to 8-9. This was extracted with 4×75 mL portions of ethyl acetate and the combined organic extracts were washed with brine and dried. The solvent was removed in vacuo to give a yellow residue that was triturated with ether to provide 1.86 g (83%) of 7 (R=iBu) as a white solid, m.p. 247°-252° (dec.); NMR (DMSO-$d_6$): δ0.90 (6H, d), 1.82 (1H, m), 3.08 (2H, t), 4.14 (1H, d, J=1 Hz), 7.56 (3H, m), 8.32 (1H, t).

Step B: Preparation of 2-(Isobutylamino)methylthieno[2,3-b]-pyrrole-5-sulfonamide hydrochloride (8 R=iBu)

To a suspension of 1.32 g (0.0348 mole) lithium aluminum hydride in 150 mL THF at room temperature was added 1.75 g (0.0058 mole) 7 (R=iBu) in 50 mL THF dropwise and the resulting mixture was heated at reflux. After 48 hours the reaction was cooled and quenched with 50 mL saturated Na⁺-K⁺ tartrate solution. After adjusting the pH of this mixture to 8-9 it was extracted with 3×200 mL ethyl acetate. The combined organic extracts were washed with brine, dried and the solvent stripped. This residue was dissolved in 3N HCl (50 mL) and extracted with ethyl acetate to remove unreacted 7 (R=iBu). The aqueous phase was then made basic (pH 8-9) and extracted with 5×50 mL portions of ethyl acetate. The combined organic extracts were washed with brine, dried and the solvent removed in vacuo to provide the free base of 7 (R=iBu) as a yellowish solid. This was dissolved in warm ethanol and treated with ethanolic HCl (1 molar equivalent) to provide 0.46 g (28%) of 8 (R=iBu) as a tan solid, m.p. 200°-203° (dec.); NMR (DMSO-$d_6$): δ0.9 (6H,d), 1.98 (1H, m), 2.70 (2H, bs), 4.26 (2H, bs), 6.61 (1H, d, J=2 Hz), 7.49 (1H, s), 7.53 (2H, bs, SO₂NH₂), 9.10 (2H, bs, —NH₂⁺), 11.65 (1H, bs).

Anal. Calc'd for C₁₁H₁₇N₃O₂S₂. HCl: C, 40.79; H, 5.60; N, 12.97. Found: C, 41.07; H, 5.64; N, 12.94.

Employing analagous synthetic methodology using an amine of structure R¹R²NH the compounds depicted in Table I are prepared:

TABLE I

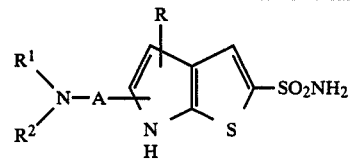

| A | R | R¹ | R² |
|---|---|----|----|
| —CH₂— | —CH₃ | —C₂H₅ | —CH₃ |
| —CH₂— | H | H | —CH₂CH₂OCH₃ |
| —CH₂— | H | —CH₂C₆H₅ | —CH₃ |
| —CH₂— | —C₂H₅ | H | H |
| —CH₂— | H | —(CH₂)₆— | |
| —CH₂— | H | —(CH₂)₃OH | —CH₃ |

TABLE I-continued

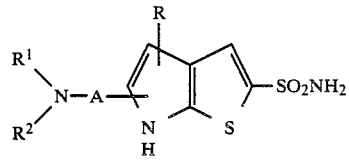

| A | R | R¹ | R² |
|---|---|---|---|
| —CH$_2$— | H | —(CH$_2$)$_2$—N—(CH$_2$)$_2$—<br>  CH$_3$ | |

EXAMPLE 3

| | | |
|---|---|---|
| 2-(Methylaminomethyl)thieno-<br>[2,3-b]pyrrole-5 sulfonamide hydrochloride | 1 mg | 15 mg |
| Monobasic sodium phosphate 2H$_2$O | 9.38 mg | 6.10 mg |
| Dibasic sodium phosphate.12H$_2$O | 28.48 mg | 16.80 mg |
| Benzalkonium chloride | 0.10 mg | 0.10 mg |
| Water for injection q.s. ad. | 1.0 ml | 1.0 ml |

The novel compound, phosphate buffer salts, and benzalkonium chloride are added to and dissolved in water. The pH of the composition is adjusted to 5.4–7.4 and diluted to volume. The composition is rendered sterile by ionizing radiation.

EXAMPLE 4

| | |
|---|---|
| 2-(Isobutylaminomethyl)thieno-<br>[2,3-b]pyrrole-5-sulfonamide hydrochloride | 5 mg |
| petrolatum q.s. ad. | 1 gram |

The compound and the petrolatum are aseptically combined.

EXAMPLE 5

| | |
|---|---|
| 2-(Isobutylaminomethyl)thieno-<br>[2,3-b]pyrrole-5-sulfonamide hydrochloride | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

or pharmaceutically acceptable salt thereof wherein

A is C$_{1-8}$ alkylene, either straight or branched chain and either unsubstituted or substituted with C$_{1-3}$ alkoxy or hydroxy; and R is hydrogen or C$_{1-6}$ alkyl either straight or branched chain;

R¹ and R² are independently:
  (1) hydrogen,
  (2) C$_{1-6}$ alkyl, either unsubstituted or substituted with one or more of
    (a) C$_{1-3}$ alkoxy,
    (b) hydroxy,
    (c) phenyl, or
    (d) —NR³R⁴ wherein R³ and R⁴ are independently selected from
      (i) hydrogen and
      (ii) C$_{1-6}$ alkyl, either unsubstituted or substituted with one or more of C$_{1-3}$ alkoxy, hydroxy or phenyl, or
  (3) taken together with the nitrogen atom to which they are attached form a 5 to 7-membered heterocycle.

2. The compound of claim 1 or a pharmaceutically acceptable salt thereof wherein R¹R²N—A— is joined to the 2-position of the thieno[2,3-b] pyrrole ring system.

3. The compound of claim 2, wherein A is —CH$_2$—.

4. The compound of claim 3, wherein R¹ is hydrogen and R² is C$_{1-6}$ alkyl.

5. The compound of claim 3 which is 2-(Isobutylaminomethyl)thieno[2,3-b]-pyrrole-5-sulfonamide or ophthalmologically acceptable salt thereof.

6. The compound of claim 3 which is 2-(Methylaminomethyl)thieno[2,3-b]-pyrrole-5-sulfonamide or ophthalmologically acceptable salt thereof.

7. An ophthalmological formulation for the treatment of ocular hypertension and glaucoma comprising an ophthalmologically acceptable carrier and an effective ocular antihypertensive amount of the compound of claim 1.

8. A method of treating ocular hypertension and glaucoma which comprises the topical ocular administration to a patient in need of such treatment of an effective ocular antihypertensive amount of the compound of claim 1.

* * * * *